United States Patent [19]

Moerker et al.

[11] Patent Number: 4,908,371
[45] Date of Patent: Mar. 13, 1990

[54] ESTERIFIED HYDROXY DIHYDROPYRIDINONES FOR TREATING DISEASES ASSOCIATED WITH TRIVALENT METAL ION OVERLOAD

[75] Inventors: Theophile Moerker, Füllinsdorf; Heinrich Peter, Binningen, both of Switzerland

[73] Assignee: Ciba-Geigy Corporation, Ardsley, N.Y.

[21] Appl. No.: 265,646

[22] Filed: Nov. 1, 1988

[30] Foreign Application Priority Data

Nov. 10, 1987 [CH] Switzerland .................. 4376/87

[51] Int. Cl.$^4$ .................. C07D 401/12; A61K 31/445
[52] U.S. Cl. ..................................... 514/318; 514/343; 514/346; 514/348; 546/193; 546/194; 546/281; 546/292; 546/296
[58] Field of Search ............... 546/256, 261, 282, 292, 546/296, 193, 194; 514/333, 335, 343, 346, 348; 518/318

[56] References Cited

U.S. PATENT DOCUMENTS

| | | | |
|---|---|---|---|
| 4,550,101 | 10/1985 | Hider et al. | 514/188 |
| 4,585,780 | 4/1986 | Hider et al. | 514/348 |
| 4,587,240 | 5/1986 | Hider et al. | 514/188 |
| 4,665,064 | 5/1987 | Hider et al. | 514/184 |
| 4,666,927 | 5/1987 | Hider et al. | 514/350 |

FOREIGN PATENT DOCUMENTS 159194  10/1985  European Pat. Off. .

Primary Examiner—Richard A. Schwartz
Assistant Examiner—Richard A. Sharpe
Attorney, Agent, or Firm—JoAnn Villamizar

[57] ABSTRACT

3-Substituted 4(1H)-pyridone compounds of formula

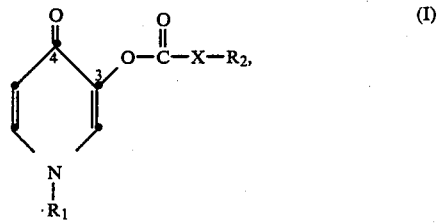

wherein $R_1$ is an unsubstituted or substituted hydrocarbon radical, X is a bond or a group of formula —O— or —N($R_3$)—, wherein $R_3$ is hydrogen or an unsubstituted or substituted hydrocarbon radical, and $R_2$ is an unsubstituted or substituted hydrocarbon radical, or wherein $R_2$ and $R_3$, when taken together, are an unsubstituted or substituted divalent hydrocarbon radical, and wherein the other ring carbon atoms of the 4(1H)-pyridinone ring, independently of one another, are unsubstituted or substituted by an unsubstituted or substituted hydrocarbon radical or by etherified or esterified hydroxy, and salts of compounds of formula I with salt-forming properties, form chelate-type metal complexes, especially with trivalent metal ions, and can be used, for example, as pharmacologically active compounds.

11 Claims, No Drawings

ESTERIFIED HYDROXY DIHYDROPYRIDINONES FOR TREATING DISEASES ASSOCIATED WITH TRIVALENT METAL ION OVERLOAD

The present invention relates to esterified azacyclic hydroxy compounds and to processes for their preparation, to the use thereof, and to pharmaceutical compositions which contain them.

The invention relates in particular to 3-substituted 4(1H)-pyridinone compounds of formula

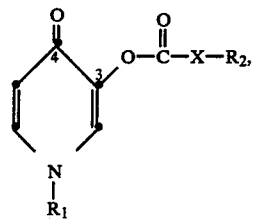

wherein $R_1$ is an unsubstituted or substituted hydrocarbon radical, X is a bond or a group of formula —O— or —N($R_3$)—, wherein $R_3$ is hydrogen or an unsubstituted or substituted hydrocarbon radical, and $R_2$ is an unsubstituted or substituted hydrocarbon radical, or wherein $R_2$ and $R_3$, when taken together, are an unsubstituted or substituted divalent hydrocarbon radical, and wherein the other ring carbon atoms of the 4(1H)-pyridinone ring, independently of one another, are unsubstituted or substituted by an unsubstituted or substituted hydrocarbon radical or by etherified or esterified hydroxy, and to salts of compounds of formula I with salt-forming properties, and also to processes for their preparation, to the use thereof, especially as pharmacologically active compounds, and to pharmaceutical compositions that contain the compounds of formula I or salts thereof with salt-forming properties.

An unsubstituted or substituted hydrocarbon radical $R_1$, $R_2$ and/or $R_3$ may be a cycloaliphatic, cycloaliphatic-aliphatic, aromatic or araliphatic hydrocarbon radical, preferably, however, an aliphatic hydrocarbon radical. Such radicals are especially alkyl such as lower alkyl or higher alkyl, also alkenyl such as lower alkenyl, or alkynyl such as lower alkynyl, as well as cycloalkyl, cycloalkenyl, cycloalkylalkyl such as cycloalkyl-lower alkyl, phenyl, naphthyl or phenylalkyl such as phenyl-lower alkyl.

An unsubstituted or substituted divalent hydrocarbon radical formed by $R_2$ and $R_3$ together is, in particular, a corresponding aliphatic hydrocarbon radical such as alkylene, for example lower alkylene.

Substituents of such hydrocarbon radicals are free, etherified or esterified hydroxy such as hydroxy, alkoxy, for example lower alkoxy, alkanoyloxy such as lower alkanoyloxy, and also a radical of formula —O—C(=O)—X—$R_2$, wherein X and $R_2$ are as defined above, as well as halogen, unsubstituted or substituted amino such as amino, and alkyl- or dialkylamino, for example lower alkylamino or di-lower alkylamino, and acylated amino such as the radical of formula —NH—C(=O)—X—$R_2$, wherein X and $R_2$ are as defined above, or free, esterified or amidated carboxy such as carboxy, alkoxycarbonyl, for example lower alkoxycarbonyl, or unsubstituted or substituted carbamoyl such as N-alkyl- or N,N-dialkylcarbamoyl, for example N-lower alkylcarbamoyl or N,N-di-lower alkylcarbamoyl.

Further, in a radical $R_1$ and $R_2$, substituents that are not linked through a carbon atom are preferably separated by at least two carbon atoms from the ring nitrogen atom or from X, provided X is other than a bond. Substituents of cyclic radicals such as cycloalkyl, cycloalkenyl, cycloalkylalkyl, phenyl, naphthyl or phenylalkyl, and of lower alkylene, may also be alkyl radicals such as lower alkyl radicals, aside from those radicals mentioned above. Substituted hydrocarbon radicals may contain one or more identical or different substituents.

An unsubstituted or substituted hydrocarbon radical $R_1$ is especially an unsubstituted or substituted aliphatic or also araliphatic hydrocarbon radical, and is more particularly alkyl such as lower alkyl, and also phenyl-lower alkyl, the substituents of such a radical being in particular free, etherified or esterified hydroxy such as lower alkoxy, as well as halogen, and also unsubstituted or substituted amino, or free, esterified or amidated carboxy. Substituents that are not linked through a carbon atom are preferably separated by at least two carbon atoms from the ring nitrogen atom.

An unsubstituted or substituted hydrocarbon radical $R_2$ is especially a corresponding aliphatic hydrocarbon radical, more particularly alkyl such as lower alkyl or higher alkyl, substituents preferably being free, esterified or amidated carboxy, preferably alkoxycarbonyl such as lower alkoxycarbonyl, and also free, etherified or esterified hydroxy or unsubstituted or substituted amino, while substituents that are not linked through a carbon atom are preferably separated by at least two carbon atoms from X, provided X is other than a bond.

A suitable radical $R_3$ is especially an aliphatic hydrocarbon radical such as alkyl, preferably lower alkyl.

A divalent aliphatic hydrocarbon radical formed by $R_2$ and $R_3$ together, in particular alkylene, preferably lower alkylene, may be substituted preferably, for example, by free, esterified or amidated carboxy, in particular alkoxycarbonyl such as lower alkoxycarbonyl.

Further unsubstituted or substituted hydrocarbon radicals as substituents of one or more than one of the other ring carbon atoms are, in particular, suitable aliphatic hydrocarbon radicals such as alkyl, preferably lower alkyl, the substituents of such radicals being preferably free, etherified or esterified hydroxy. Free, etherified or esterified hydroxy groups as substituents of further ring carbon atoms are preferably lower alkoxy and halogen.

In connection with the foregoing description, the general terms employed therein have the following preferred meanings:

Definitions qualified by the term "lower" will be understood as meaning organic radicals and compounds containing up to 8 carbon atoms inclusive, for example up to 3, preferably up to 4, carbon atoms inclusive.

Alkyl may be lower alkyl such as lower alkyl of up to 3 carbon atoms inclusive, for example n-propyl or isopropyl, preferably methyl, as well as ethyl, n-propyl or isopropyl, or lower alkyl of 4 to 8 carbon atoms inclusive, for example n-butyl, isobutyl, sec-butyl, tert-butyl, n-pentyl, neopentyl, n-hexyl, n-heptyl or n-octyl, or also higher alkyl, preferably of 9 to 16 carbon atoms inclusive, for example n-nonyl, n-decyl, n-undecyl or n-dodecyl.

Alkenyl and alkynyl are preferably lower alkenyl and lower alkynyl, respectively, each of up to 8 carbon atoms inclusive, preferably of up to 4 carbon atoms inclusive, for example allyl, methallyl or propargyl.

In cycloalkyl, cycloalkenyl and cycloalkylalkyl radicals, wherein alkyl is preferably lower alkyl, a cycloalkyl radical preferably contains 3 to 8, preferably 5 or 6, ring carbon atoms, and a cycloalkenyl radical contains preferably 5 or 6 ring carbon atoms. Examples of such radicals are cyclopropyl, cyclopentyl, cyclohexyl, 1-cyclohexenyl, cyclopropylmethyl, cyclopentylmethyl, cyclohexylmethyl or cyclohexylethyl.

In a phenylalkyl radical, alkyl is preferably lower alkyl. Suitable groups are, for example, benzyl or 1 or 2-phenylethyl.

Lower alkylene contains preferably 3 to 5 carbon atoms inclusive in the chain and is, for example, 1,3-propylene, 1,4-butylene or 1,5-pentylene.

Lower alkoxy is, for example, methoxy, ethoxy, n-propoxy, isopropoxy or n-butoxy; and lower alkanoyloxy is, for example, acetoxy or propionyloxy, and halogen (hydroxy esterified with hydrohalic acid) is preferably chloro, and also fluoro or bromo as well as iodo.

Lower alkylamino and di-lower alkylamino are, for example, methylamino, ethylamino, dimethylamino or diethylamino.

Lower alkoxycarbonyl is, for example, methoxycarbonyl, ethoxycarbonyl, propoxycarbonyl or isopropoxycarbonyl; and N-lower alkylcarbamoyl and N,N-di-lower alkylcarbamoyl are, for example, N-methylcarbamoyl, N-ethylcarbamoyl, N,N-dimethylcarbamoyl or N,N-diethylcarbamoyl.

Salts of compounds of formula I with salt-forming properties are, in particular, pharmaceutically acceptable salts, preferably with salt-forming acids such as mineral acids, for example hydrochloric acid or sulfuric acid, or strong organic carboxylic acids or sulfonic acids, for example acetic acid, fumaric acid, embonic acid or methanesulfonic acid, or also with salt-forming bases, provided such compounds contain, for example, free carboxyl groups as substituents, for example alkali metal salts or alkaline earth metal salts such as sodium, potassium or calcium salts, or ammonium salts.

Depending on the structural conditions, the compounds of this invention can be obtained in the form of mixtures of isomers or of pure isomers.

The novel compounds have useful, especially pharmacologically useful, properties. Thus, for example, they can be converted under in vivo conditions into the corresponding 3-hydroxy-4(1H)-pyridinone compounds, which form stable chelate-type metal complexes, especially with trivalent metal ions such as chromium(III) ions, aluminium ions and, most particularly, iron(III) ions. For example, as can be demonstrated in an animal model using non-iron overloaded bile duct cannulated rats, the novel compounds in doses from about 5 mg/kg are able to prevent the deposition of iron-containing pigments in the tissue and to effect excretion of iron where iron deposits are present in the orgaism, for example where these occur in hemochromatosis, haemosiderosis, cirrhosis of the liver, and poisoning caused by compounds of trivalent ions. The novel compounds can therefore be used as pro-drugs for the corresponding 3-hydroxy-4-(1H)-pyridinone compounds in the treatment of diseases and pathological conditions of the human and animal body that are associated with excessive iron overloading of the organism such as major thalassaemia, sickle-cell anaemia, sideroacrestic anaemia, aplastic anaemia and further forms of anaemia in which haemisiderosis (i.e. a local or general increase in the reverses of iron in otherwise intact body tissues) is a factor. To this type belong also pathological conditions which develop in patients after repeated blood transfusions or repeated dialysis treatment for loss of, or impaired, kidney function. The novel compounds can also be used for the treatment of diseases caused by iron(III)-dependent microorganisms and parasites, especially malaria. Further, the complex formation of the corresponding 3-hydroxy-4(1H)-pyridinones with other trivalent metals can be used for their excretion from the organism, for example for removing aluminium in dialysis encaphalopathy and osteomalacia, as well as in Alzheimer's disease. Compared with the corresponding 3-hydroxy-4(1H)-pyridinone compounds, the novel compounds of the present invention are effective when administered orally and are well tolerated, and they have a long-lasting action.

The invention relates in particular to compounds of formula I, wherein X is as defined above, and $R_1$, $R_2$ and $R_3$ are independently of one another an aliphatic, cycloaliphatic, cycloaliphatic-aliphatic, aromatic or araliphatic hydrocarbon radical which is unsubstituted or substituted by free, etherified or esterified hydroxy, unsubstituted or substituted amino and/or free, esterified or amidated carboxy, and $R_3$ can also be hydrogen, or wherein $R_1$ is as defined above, and $R_2$ and $R_3$, when taken together, are a divalent aliphatic hydrocarbon radical which is unsubstituted or substituted by free, etherified or esterified hydroxy, unsubstituted or substituted amino, and/or free, esterified or amidated carboxy, and wherein the other ring carbon atoms of the 4(1H)-pyridinone ring, independently of one another, are unsubstituted or can carry as substituents aliphatic, cycloaliphatic, cycloaliphatic-aliphatic, aromatic or araliphatic hydrocarbon radicals containing free, etherified or esterified hydroxy, unsubstituted or substituted amino or free, esterified or amidated carboxy, or free, etherified or esterified hydroxy, and salts, especially pharmaceutically suitable salts, of such compounds with salt-forming properties.

The invention relates more particularly to compounds of formula I, wherein X is as defined above, $R_1$ and $R_2$ are each independently of the other alkyl, for example lower alkyl or higher alkyl, cycloalkyl, cycloalkenyl, cycloalkyl-lower alkyl, phenyl, naphthyl or phenyl-lower alkyl, which radicals are unsubstituted or substituted by hydroxy, lower alkoxy, lower alkanoyloxy, the radical of formula —O—C(=O)—X—$R_2$, wherein X and $R_2$ have the given meanings, and also by halogen, amino, lower alkylamino, di-lower alkylamino, carboxy, lower alkoxycarbonyl, carbamoyl, lower alkylcarbamoyl and/or di-lower alkylcarbamoyl, $R_3$ is hydrogen or lower alkyl, or wherein $R_1$ is as defined above, and $R_2$ and $R_3$, when taken together, are lower alkylene which is unsubstituted or is substituted by hydroxy, lower alkoxy, lower alkanoyloxy, the radical of formula —O—C(=O)—X—$R_2$, wherein X and $R_2$ have the given meanings, and also by halogen, amino, lower alkylamino, di-lower alkylamino, carboxy, lower alkoxycarbonyl, carbamoyl, lower alkylcarbamoyl and/or di-lower alkylcarbamoyl, and wherein the other ring atoms of the 4(1H)-pyridinone ring, independently of one aother, are unsubstituted or are substituted preferably in the 2- or 6-position by alkyl, preferably lower alkyl, which is unsubstituted or substituted by hydroxy, lower alkoxy, esterified hydroxy of formula —O—C(=O)—X—$R_2$, wherein X and R₂ have the given meanings, and/or by halogen, and salts, especially pharmaceutically acceptable salts, of such compounds with a salt-forming properties.

The invention relates preferably to compounds of formula I, wherein X is as defined above, R₁ is lower alkyl of preferably up to 4 carbon atoms inclusive which is unsubstituted or is substituted in a position higher than the 1-position by lower alkoxy of preferably up to 4 carbon atoms inclusive, for example methoxy or ethoxy, R₂ is lower alkyl of preferably up to 8 carbon atoms inclusive, for example methyl, and also ethyl, n-propyl or n-heptyl, which is unsubstituted or substituted by lower alkoxycarbonyl, wherein lower alkoxy preferably contains up to 4 carbon atoms inclusive, for example methoxycarbonyl or ethoxycarbonyl, and R₃ is hydrogen or lower alkyl, preferably of up to 4 carbon atoms inclusive, for example methyl or ethyl, or wherein R₁ is as defined above, and R₂ and R₃, when taken together, are lower alkylene containing 4 or 5 carbon atoms in the chain which is unsubstituted or substituted, preferably in 1-position, by lower alkoxycarbonyl, wherein lower alkoxy preferably contains up to 4 carbon atoms inclusive, for example methoxycarbonyl or ethoxycarbonyl, and wherein the other ring carbon atoms of the 4(1H)-pyridinone ring, independently of one another, are unsubstituted or are substituted preferably in 6-position or, most preferably in 2-position, by lower alkyl of preferably up to 4 carbon atoms inclusive, especially methyl, and also ethyl, which is unsubstituted or substituted by hydroxy, lower alkoxy of preferably up to 4 carbon atoms inclusive, for example methoxy or ethoxy, a radical of formula —O—C(=O)—X—R₂, wherein X and R₂ have the given meanings, or by halogen, for example chloro, and salts, especially pharmaceutically acceptable salts, of such compounds with salt-forming properties.

The invention relates most particularly to compounds of formula I, wherein R₁ is lower alkyl of up to 4 carbon atoms inclusive, for example methyl, ethyl, n-propyl, isopropyl or n-butyl, which may be substituted in a position higher than 1-position by lower alkoxy of up to 4 carbon atoms inclusive, for example methoxy or ethoxy (i.e. lower alkoxy is separated from the ring nitrogen atom by at least two carbon atoms), and wherein X is a direct bond and R₂ is lower akyl of 4 to 8 carbon atoms inclusive, for example tert-butyl or n-heptyl, or X is a group of formula —O— and R₂ is lower alkyl of up to 4 carbon atoms inclusive, or preferably X is a group of formula —N(R₃)—, wherein R₃ is preferably hydrogen, and also lower alkyl of up to 4 carbon atoms inclusive, for example methyl or ethyl, and R₂ is lower alkyl of up to 4 carbon atoms inclusive, preferably methyl, which is unsubstituted or substituted by lower alkoxycarbonyl of up to 5 carbon atoms inclusive, for example methoxycarbonyl or ethoxycarbonyl, or wherein R₂ and R₃, when taken together, are lower alkylene containing 4 or 5 carbon atoms in the chain which is unsubstituted or is substituted, preferably in 1-position, by lower alkoxycarbonyl of up to 5 carbon atoms inclusive, for example methoxycarbonyl or ethoxycarbonyl, and wherein the 2-position is substituted by lower alkyl of up to 4 carbon atoms inclusive, for example methyl, and also ethyl, or salts, especially pharmaceutically acceptable salts, of such compounds with salt-forming properties.

The invention relates first and foremost to the individual compounds described in the Examples.

The compounds of this invention can be prepared in a manner known per se, preferably by reacting the hydroxy group of a compound of formula

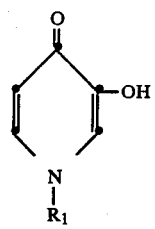
(II)

wherein R₁ is as defined above and other ring carbon atoms of the 4(1H)-pyridinone ring are unsubstituted or substituted as indicated above, or of a reactive derivative thereof, by treatment with an acylating agent that introduces the acyl radical of formula —C(=O)—X—R₂, in which X and R₂ have the above given meaning, and, if desired, converting a resultant salt into the free compound and/or a resultant free, salt-forming compound into a salt, and/or resolving a resultant mixture of isomers into the individual isomers.

Reactive derivatives of compounds of formula I are preferably corresponding salts such as acid addition salts, for exaple with suitable mineral acids such as hydrochloric acid.

The esterification of the hydroxy group can be effected in a manner known per se, preferably by reacting the starting material of formula II with an acid corresponding to the acyl radical of formula —(C=O)—X—R₂ or with a suitable reactive derivative thereof.

Reactive derivatives of the corresponding acids are preferably suitable anhydrides such as symmetrical, mixed and inner anhydrides of such acids. By mixed anhydrides are meant, in particular, the mixed anhydrides with strong inorganic acids, preferably hydrohalic acids such as hydrobromic acid and, most preferably, hydrochloric acid (i.e. the corresponding acid halides such as acid bromides and, preferably, acid chlorides), further with hydrocyanic acid, as well as those with half-esters of carbonic acid such as corresponding lower alkyl half-esters, for example methyl half-esters, ethyl half-esters, or isobutyl half-esters, of carbonic acid (obtained, for example, by treating a suitable salt of the acid, such as an ammonium salt, with a corresponding ester of chloroformic acid), or with suitably substituted lower alkanecarboxylic acids, preferably a halogen-substituted acetic acid, for example trichloroacetic acid (obtained for example by treating the acid or a suitable salt thereof with the corresponding acid halide, for example the acid chloride). Inner anhydrides are, for example, the corresponding ketenes or, as inner anhydrides of carbamic acid compounds, the corresponding isocyanate compounds.

Further reactive acid derivatives are activated esters, such as esters of vinylogous alcohols (i.e. enols), for example esters with vinylogous lower alkanols, with N-hydroxyimide compounds such as N-hydroxysuccinimide, with lower alkanols containing an electrophilic group, for example cyanomethanol, or with suitably substituted phenols, for example pentachlorophenol or 2,4-dinitrophenol.

The acylation reaction is normally carried out in the presence of condensing agents. If the starting material is the free acid, suitable hydrophilic agents and also carbodiimides, for example dicyclohexylcarbodiimide, are used, whereas if the starting material is a derivative, particularly a salt, it is preferred to use an acid acceptor, preferably a suitable organic base, for example triethylamine or pyridine. The reaction is preferably carried out in the presence of suitable solvents or mixtures thereof, although acid acceptor bases may also be suitably employed, if necessary with cooling or heating, in a closed vessel and/or in an inert gas atmosphere, for example nitrogen or argon.

In addition to the 3-hydroxy group, it is also possible to acylate other hydroxy and/or amino groups present in the starting material. In this connection, hydroxy groups located in different positions can be acylated stepwise. Thus, for example, hydroxy groups present in side-chains, compared with the 3-hydroxy group, can normally only be acylated after this latter and for this reason only by using an excess of acylating agent.

The starting materials of formula II are known or can be prepared in a manner known per se.

Salts of compounds of formula I can be converted in a manner known per se into the free compounds: acid addition salts by treatment with a basic agent, such as an inorganic base, for example an alkali metal or alkaline earth metal such as sodium or potassium hydroxide, sodium or potassium carbonate or sodium or potassium bicarbonate, and salts with bases by treatment with an acid reagent such as a mineral acid, for example hydrochloric acid or sulfuric acid.

Free compounds of formula I can be converted in a manner known per se into their salts: compounds with basic properties by treatment with acids or suitable derivatives thereof, and compounds with acid properties by treatment with a suitable base or a derivative thereof.

Mixtures of isomers can be resolved in a manner known per se into the individual isomers: racemates, for example, by forming salts with optically pure salt-forming reagents and resolving the mixture of diastereoisomers so obtained, for example by fractional crystallisation.

In the process of this invention it is preferred to use those starting materials that lead to the compounds described at the outset as being especially useful.

The invention relates to those embodiments of the process in which a compound obtainable as intermediate at any stage of the process is used as starting material and the remaining steps are carried out, or in which a starting material is formed under the reaction conditions or is used in the form of a derivative, for example a salt thereof.

The present invention also relates to pharmaceutical compositions which contain one of the pharmacologically active compounds of formula I or a salt thereof as active ingredient. Compositions for enteral, especially oral as well as parenteral, administration are preferred. The compositions contain the active ingredient alone or, preferably, together with a pharmaceutically acceptable carrier. The dosage of the active ingredient depends on the disease to be treated, as well as on the species, age, weight and individual conditon of the patient and also on the mode of application.

The pharmaceutical compositions contain from ca. 5% to ca. 95% of the active ingredient, formulations in single dosage unit form containing preferably ca. 20% to ca. 90% of active ingredient, and formulations not in single dosage unit form preferably containing ca. 5% to ca. 20% of active ingredient. Dosage unit forms such as dragées, tablets or capsules contain from ca. 0.05 g to ca. 1.0 g of active ingredient.

The pharmaceutical compositions of this invention are prepared in a manner known per se, for example by conventional mixing, granulating, confectioning, dissolving or lyophilising methods. For exaple, pharmaceutical compositions for oral administration can be obtained by combining the active ingredient with solid carriers, optionally granulating a resulting mixture and processing the mixture or granulate, if desired or necessary after the addition of suitable excipients, to tablets or dragée cores.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or polyvinylpyrrolidone, and/or, if desired, disintegrators, such as the above-mentioned starches, also carboxymethyl starch, crosslinked polyvinylpyrrolidone, agar, alginic acid or a salt thereof such as sodium alginate. Excipients are in particular glidants and lubricants, for example silica, talcum, stearic acid or salts thereof such as magnesium stearate or calcium stearate, and/or polyethylene glycol. Dragée cores can be provided with suitable coatings which are non-resistant or resistant to gastric juices, using, for example, concentrated sugar solutions which may contain gum arabic, talcum, polyvinylpyrrolidone, polyethylene glycol and/or titanium dioxide, shellac solutions in suitable organic solvents or mixtures of solvents or, for the preparation of coatings which are resistant to gastric juices, solutions of suitable cellulose preparations such as acetyl cellulose phthalate or hydroxypropyl methyl cellulose phthalate. Dyes or pigments can be added to the tablets or dragée coatings, for example to identify or indicate different doses of active ingredient.

Further pharmaceutical compositions for oral administration are dry-filled capsules made of gelatin and also soft sealed capsules consisting of gelatin and a plasticiser such as glycerol or sorbitol. The dry-filled capsules can contain the active ingredient in the form of granules, for example in admixture with fillers such as lactose, binders such as starches, and/or glidants such as talcum or magnesium stearate, and optionally stabilisers. In soft capsules, the active ingredient is preferably dissolved or suspended in a suitable liquid, such as a fatty oil, paraffin oil or a liquid polyethylene glycol, to which a stabiliser can also be added.

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethylene glycols and higher alkanols.

Particularly suitable dosage forms for parenteral administration are aqueous solutions of an active ingredient in water-soluble form, for example a water-soluble salt, or aqueous injection suspensions which contain substances which increase the viscosity, for example sodium carboxymethyl cellulose, sorbitol and/or dextran, and optionally stabilisers. In addition, the active ingredient, with or without adjuvants, can also be in lyophilised form and brought into solution prior to parenteral administration by addition of suitable solvents.

The solutions used, for example, for parenteral administration can also be used as infusion solutions.

The invention further relates to a method of treating pathological conditions which, as described above, are associated with an excess of, for example, iron(III) or aluminium in the body. The compounds of this invention can be administered prophylactically or therapeutically, and are preferably administered in the form of pharmaceutical compositions. A daily dose of ca. 0.1 g to ca. 10 g, preferably from ca. 0.5 g to ca. 5 g, of a compound of the invention will be administered to a warm-blooded animal having a body weight of ca. 70 kg.

The invention is illustrated by the following Examples.

EXAMPLE 1

With stirring, 1.4 ml of triethylamine 1.7 ml of ethyl isocyanatoacetate are added at room temperature to a suspension of 1.39 g of 3-hydroxy-1,2-dimethyl-4(1H)-pyridinone in 100 ml of acetonitrile and 100 ml of methylene chloride, followed by the addition of 1.7 ml of ethyl isocyanatoacetate. The ensuing reaction is slightly exothermic. The solution that forms after about 15 minutes is concentrated by evaporation under reduced pressure after a further 45 minutes. The residue is dried under a high vacuum and crystallized from a mixture of methylene chloride and ethyl acetate. The crude crystalline product is taken up in 10 ml of methanol, insoluble material is removed by filtration, and the filtrate is concentrated by evaporation under reduced pressure. The residue is crystallised from a mixture of methylene chloride/ethyl acetate, affording 3-(ethoxycarbonylmethylaminocarbonyloxy)-1,2-dimethyl-4(1H)-pyridinone with a melting point of 132°–135° C.

EXAMPLE 2

With stirring, 11.2 ml of triethylamine are added at room temperature to a suspension of 5.56 g of 3-hydroxy-1,2-dimethyl-4(1H)-pyridinone in 100 ml of acetonitrile and 100 ml of methylene chloride, followed by the addition of 7.64 ml of ethyl chloroformate. Within 15 minutes a complete solution forms and, after a further 45 minutes, the volatile constituents are removed by evaporation under reduced pressure. The residue is dried under a high vacuum and the unreacted starting material is crystallised from ethyl acetate. 3-Ethoxycarbonyloxy-1,2-dimethyl-4(1H)-pyridinone is obtained from the mother liquor in the form of a yellow foam with a melting point of 113°–115° C.; thin-layer chromatogram: Rf=0.05 (7:3 mixture of methylene chloride and acetone), 0.10 (9:1 mixture of methylene chloride and isopropanol, 0.20 (9:1 mixture of methylene chloride and methanol), and 0.35 (4:1 mixture of methylene chloride and methanol).

EXAMPLE 3

With stirring, 0.56 ml of triethylamine is added at room temperature to a suspension of 0.556 g of 3-hydroxy-1,2-dimethyl-4(1H)-pyridinone in 40 ml of acetonitrile and 40 ml of methylene chloride, followed by the addition of 1.02 ml of caprylyl chloride. A solution forms within 3 minutes and after 30 minutes the reaction is complete, and the volatile constituents are removed by evaporation under reduced pressure. The residue is dried under a high vacuum and crystallised from a mixture of methylene chloride and ethyl acetate. The 3-(n-octanoyloxy)-1,2-dimethyl-4-(1H)-pyridinone so obtained begins to sinter at 140° C. and decomposes at 180° C.

EXAMPLE 4

With stirring, 0.56 ml of triethylamine is added at room temperature to a suspension of 0.556 g of 3-hydroxy-1,2-dimethyl-4(1H)-pyridinone in 40 ml of acetonitrile and 40 ml of methylene chloride, followed by the addition of 0.76 ml of diethylcarbamoyl chloride. The suspension still remains intact after 60 minutes and thin-layer chromatography shows that no reaction has taken place. Then 20 ml of pyridine are added to the mixture, which turns yellowish in colour. After a further 60 minutes the onset of reaction can be observed. This reaction is brought to completion by stirring for 16 hours. The volatile constituents are removed by evaporation under reduced pressure. The residue is dried under a high vacuum, then dissolved in methanol, and the solution is treated with activated carbon, filtered and concentrated by evaporation. The filtrate is taken up in 100 ml of ethyl acetate, whereupon a product crystallises. A furthher crystalline product can be obtained by working up the mother liquor. The two products are combined and dissolved in methylene chloride. The solution is washed twice with water and the organic phase is concentrated by evaporation. The residue is crystallised from ethyl acetate, affording 3-(diethylaminocarbonyloxy)-1,2-dimethyl-4(1H)-pyridinone with a melting point of 135°–137° C.

EXAMPLE 5

With stirring, 8.4 ml of triethylamine are added at room temperature to a suspension of the hydrobromide salt of 3-hydroxy-1,2-dimethyl-4(1H)-pyridinone in 100 ml of acetonitrile and 100 ml of methylene chloride, followed by the addition of 80 ml of a solution of ethyl 3-isocyanatopropionate in toluene (freshly prepared from β-alanine ethyl ester hydrochloride and phosgene by the process described below). A solution forms within 30 minutes. After a further 30 minutes the reaction is complete and the volatile constituents are removed by evaporation under reduced pressure. The residue is dried under a high vacuum and crystallised from ethyl acetate, affording the hydrobromide of 3-[(2-ethoxycarbonylethyl)aminocarbonyloxy]-1,2-dimethyl-4(1H)-pyridinone of m.p. 153°–154° C., which is dissolved in 100 ml of water. The solution is adjusted to pH 7.5 by addition of sodium bicarbonate and then extracted with methylene chloride. The residue of the organic extract is recrystallised from ethyl acetate, affording 3-[(2-ethoxycarbonylethyl)aminocarbonyloxy]-1,2-dimethyl-4(1H)-pyridinone with a melting point of 171°–173° C.

The solution of ethyl 3-isocyanatopropionate in toluene used in the above process can be prepared as follows: A mixture of 15.36 g of β-alanine ethyl ester in 600 ml of toluene is dissolved by heating to 90° C. Then 63 ml of a 20% solution of phosgene in toluene are added over 10 minutes under argon and at a temperature of 90°–95° C. Stirring at ca. 90° C. for 16 hours gives the desired solution of ethyl isocyanatopropionate, which is used direct in the above reaction.

EXAMPLE 6

1.40 ml of triethylamine are added to a suspension of 0.945 g of the hydrochloride of 1-ethyl-3-hydroxy-2-methyl-4(1H)-pyridinone in 30 ml of acetonitrile and 30 ml of methylene chloride, and 1.135 ml of ethyl isocyanatoacetate are added to the mixture. The ensuring reaction is slightly exothermic, and after 10 minutes a solution forms. The reaction is complete after 1.5 hours. The reaction mixture is evaporated to dryness under reduced pressure, and the residue is dried under a high vacuum and crystallised from ethyl acetate, to give the hydrochloride of 1-ethyl-3-(ethoxycarbonylmethylaminocarbonyloxy)-2-methyl-4(1H)-pyridinone of m.p. 154°–156° C. (contains some triethylamine). 2 g of the salt are dissolved in 20 ml of water, the solution is adjusted to pH 2.5 with phosphoric acid and saturated with sodium chloride, and then extracted with methylene chloride. The residue of the organic extract is recrystallised from a 95:5 mixture of ethyl acetate and methylene chloride, giving 1-ethyl-3-(ethoxycarbonylmethylaminocarbonyloxy)-2-methyl-4-(1H)-pyridinone which melts at 102°–103° C.

The starting material can be prepared as follows: To a solution of 21.62 g of 3-benzyloxy-2-methyl-4H-pyran-4-one in 500 ml of methanol are added 10.19 g of ethylamine hydrochloride in 200 ml of water followed by the addition of 8.0 g of sodium hydroxide in 100 ml of methanol. The clear yellow solution is refluxed for 5 hours and stirred, then concentrated by evaporation under reduced pressure. The residue is taken up in methylene chloride, and the solution is washed with water and added to a column of silica gel. The amorphous 3-benzyloxy-1-ethyl-2-methyl-4(1H)-pyridinone is eluted with a 9:1 mixture of methylene chloride and methanol and taken up in 100 ml of concentrated hydrochloric acid. The mixture is refluxed for 3 minutes, whereupon a solution forms. This solution is concentrated by evaporation with addition of isopropanol, and the residue is crystallised from isopropanol and washed with ethyl acetate. The hydrochloride of 1-ethyl-3-hydroxy-2-methyl-4(1H)-pyridinone melts at 196°–198° C.

EXAMPLE 7

2.80 ml of triethylamine 2.27 ml of ethyl isocyanoacetate are added at room temperature to a suspension of 2.036 g of 3-hydroxy-2-methyl-1-n-propyl-4(1H)-pyridinone hydrochloride in 50 ml of acetonitrile and 50 ml of methylene chloride, followed by the addition of 2.27 ml of ethyl isocyanoacetate. The reaction is slightly exothermic and a solution forms within 10 minutes. The reaction is complete after 1.5 hours. The solution is evaporated to dryness under reduced pressure, the residue is dried under a high vacuum and crystallised from ethyl acetate, affording the hydrochloride of 3-(ethoxycarbonylmethylaminocarbonyloxy)-2-methyl-1-n-propyl-4(1H)-pyridinone which melts at 139°–141° C. and is contaminated with triethylamine hydrochloride.

A solution of 4.1 g of the salt in 40 ml of water is adjusted to pH 2.5 with phosphoric acid, saturated with sodium chloride and extracted with methylene chloride. The residue of the organic extract is crystallised from a 95:5 mixture of ethyl acetate and methylene chloride, affording 3-(ethoxycarbonylmethylaminocarbonyloxy)-2-methyl-1-n-propyl-4(1H)-pyridinone with a melting point of 96°–97° C.

The starting material can be prepared as follows: 20.64 ml of n-propylamine are added to a solution of 43.24 g of 3-benzyloxy-2-methyl-4H-pyran-4-one in 1000 ml of methanol, followed by the addition of 12.0 g of sodium hydroxide in 100 ml of methanol. The reaction mixture is refluxed for 3 hours, then concentrated by evaporation. The residue is taken up in methylene chloride and the organic solution is washed with water. The phases are clarified by addition of a saturated solution of sodium chloride in water, and the organic extract is dried over sodium sulfate and concentrated by evaporation under reduced pressure. The residue is dried under a high vacuum, giving 3-benzyloxy-2-methyl-1-n-propyl-4(1H)-pyridinone as an oily product.

A solution of 10 g of 3-benzyloxy-2-methyl-1-n-propyl-4(1H)-pyridinone in 100 ml of concentrated (37%) aqueous hydrochloric acid is refluxed for 5 minutes, whereupon initially a precipitate forms that dissolves again. The reaction product is diluted with isopropanol and the solution is concentrated by evaporation under reduced pressure until the formation of crystalline material. This crystalline material is recrystallised from ethyl acetate and gives 3-hydroxy-2-methyl-1-n-propyl-4(1H)-pyridinone hydrochloride which melts at 205°–207° C.

EXAMPLE 8

2.8 ml of triethylamine are added at room temperature to a suspension of 1.89 g of 2-ethyl-3-hydroxy-1-methyl-4(1H)-pyridinone hydrochloride in 50 ml of acetonitrile and 50 ml of methylene chloride followed by the addition of 2.27 ml of ethyl isocyanatoacetate. The ensuing reaction is slightly exothermic and a solution forms within 10 minutes. The reaction is complete after 1.5 hours. The reaction mixture is evaporated to dryness under reduced pressure, the residue is dried under a high vacuum and crystallised from ethyl acetate. A solution of 4.0 g of the resultant hydrochloride of 3-(ethoxycarbonylmethylaminocarbonyloxy)-2-ethyl-1-methyl-4(1H)-pyridinone in 40 ml of water is adjusted to pH 2.5 with phosphoric acid, saturated with sodium chloride and extracted with methylene chloride. The residue of the organic extract is crystallised from a 95:5 mixture of ethyl acetate and methylene chloride, affording 3-(ethoxycarbonylmethylaminocarbonyloxy)-2-ethyl-1-methyl-4(1H)-pyridinone with a melting point of 99°–100° C.

The starting material can be prepared as follows: 108 g of sodium hydroxide in 400 ml of water are added to a mixture of 350 g of 2-ethyl-3-hydroxy-4H-pyran-4-one in 3000 ml of methanol, and the colourless solution is treated with 336 ml of benzyl chloride. The reaction mixture is refluxed for 6 hours, stirred for a further 16 hours at room temperature, and the solvent is removed by evaporation. The residue is taken up in 1000 ml of a phosphate buffer solution (pH 8.5) and extracted with 2×600 ml of methylene chloride. The residue obtained from the extract can be purified by chromatography over silica gel with methylene chloride as eluant or by distillation.

To a solution of 23 g of the resultant 3-benzyloxy-2-ethyl-4H-pyran-4-one in 500 ml of methanol are added 8.44 g of methylamine hydrochloride in 200 ml of water, followed by the addition of 8.5 g of sodium hydroxide. The reaction mixture is stirred for 3 days at room temperature, then concentrated by evaporation under reduced pressure, and the residue is taken up in methylene chloride. The insoluble constituent is discarded. The clear solution is chromatographed over silica gel, and elution is effected with a 97:3 mixture of methylene chloride and methanol.

The 3-benzyloxy-2-ethyl-1-methyl-4(1H)-pyridinone so obtained is taken up in 100 ml of concentrated aqueous hydrochloric acid and the mixture is refluxed for 5 minutes, whereupon a solution forms. This solution is concentrated by evaporation with the addition of isopropanol, and the resultant 2-ethyl-3-hydroxy-1-methyl-4(1H)-pyridinone hydrochloride is crystallised from isopropanol and washed with ethyl acetate. Melting point: 178°–179° C.

EXAMPLE 9

5.60 ml of triethylamine are added to a mixture of 5.49 g of 3-hydroxy-1-(2-methoxyethyl)-2-methyl-4(1H)-pyridinone in 150 ml of acetonitrile and 150 ml of methylene chloride, followed by the addition of 6.83 ml of ethyl isocyanatoacetate at room temperature. The slightly exothermic reaction, in the course of which a solution forms within 10 minutes, is complete after 3 hours. The solvent is removed under reduced pressure and the residue is dried under a high vacuum and crystallised from ethyl acetate. The mother liquor is discarded. 1 g of the pale beige product is partitioned between methylene chloride and water. The bulk of the product is present in the aqueous phase, which is concentrated by evaporation. The residue is dissolved in methanol and the solution is treated with activated carbon and concentrated by evaporation. The residue is crystallised from ethyl acetate, to give white crystalline 3-(ethoxycarbonylmethylaminocarbonyloxy)-1-(2-methoxyethyl)-2-methyl-4(1H)-pyridinone with a melting point of 134°–135° C.

The starting material can be prepared as follows: A solution of 43.24 g of 3-benzyloxy-2-methyl-4H-pyran-4-one in 800 ml of methanol is treated with 21.9 ml of 2-methoxyethylamine (98%) and then with a solution of 12.0 g of sodium hydroxide in 100 ml of methanol. The yellow solution is refluxed for 5 hours and, after addition of a further 4.4 ml of 2-methoxyethylamine, refluxed for a further 1 hour. After cooling, the reaction mixture is concentrated by evaporation under reduced pressure. The residue is taken up in methylene chloride, and the solution is washed with water and concentrated by evaporation.

A mixture of 18.0 g of the 3-benzyloxy-1-(2-methoxyethyl)-2-methyl-4(1H)-pyridinone so obtained and 100 ml of fuming aqueous hydrochloric acid is refluxed for 2 minutes, cooled, diluted with isopropanol, and concentrated by evaporation under reduced pressure. The 3-hydroxy-1-(2-methoxyethyl)-2-methyl-4(1H)-pyridinone hydrochloride obtained as crystalline residue is further purified by recrystallisation from ethyl acetate and isopropanol.

A solution of 5 g of the above salt in 50 ml of water is adjusted to pH 7.0 with solid sodium hydroxide, and the free 3-hydroxy-1-(2-methoxyethyl)-2-methyl-4(1H)-pyridinone hydrochloride is extracted with 3×200 ml of methylene chloride. The residue melts at 178°–179° C. after recrystallisation from ethyl acetate.

EXAMPLE 10

2.80 ml of triethylamine are added to a suspension of 2.477 g of 1-(3-ethoxypropyl)-3-hydroxy-2-methyl-4(1H)-pyridinone hydrochloride in 50 ml of acetonitrile and 50 ml of methylene chloride, followed by the addition at room temperature of 2.27 ml of ethyl isocyanatoacetate. A solution forms within 10 minutes and the reaction is complete after 1.5 hours. The volatile constituents are removed under reduced pressure, and the residue is dried under a high vacuum and crystallised from ethyl acetate.

A solution of 4.0 g of the resultant 3-(ethoxycarbonylmethylaminocarbonyloxy)-1-(3-ethoxypropyl)-2-methyl-4(1H)-pyridinone hydrochloride, which melts at 92°–93° C. and is contaminated with a small amount of triethylamine hydrochloride, in 40 ml of water is adjusted to pH 2.5 with phosphoric acid, saturated with sodium chloride, and extracted with methylene chloride. The residue is recrystallised from a 95:5 mixture of ethyl acetate and methylene chloride, giving 3-(ethoxycarbonylmethylaminocarbonyloxy)-1-(3-ethoxypropyl)-2-methyl-4(1H)-pyridinone, which melts at 84°–85° C.

The starting material can be prepared as follows: To a solution of 21.62 g of 3-benzyloxy-2-methyl-4H-pyran-4-one in 500 ml of methanol are added 15.0 ml of 3-ethoxypropylamine, followed by the addition of a solution of 6.0 g of sodium hydroxide in 100 ml of methanol. The clear yellow solution is stirred for 5 hours, with heating, to reflux, then concentrated by evaporation under reduced pressure. The residue is taken up in methylene chloride and the solution is washed with water and chromatographed over silica gel with a 9:1 mixture of methylene chloride and methanol as eluant.

The amorphous 3-benzyloxy-1-(3-ethoxypropyl)-2-methyl-4(1H)-pyridinone so obtained is taken up in 100 ml of concentrated aqueous hydrochloric acid and refluxed for 3 minutes. The solution so obtained is diluted with isopropanol and evaporated to dryness. The residue is crystallised from isopropanol and washed with ethyl acetate, affording 1-(3-ethoxypropyl)-3-hydroxy-2-methyl-4(1H)-pyridinone hydrochloride which melts at 130°–131° C.

EXAMPLE 11

2.80 ml of triethylamine are added to a suspension of 2.78 g of 1,2-dimethyl-3-hydroxy-4(1H)-pyridinone in 100 ml of pyridine and 100 ml of acetonitrile, and then a hot solution of 1-chlorocarbonyl-L-proline methyl ester hydrochloride (prepared by reacting a solution of 0.99 g of L-proline methyl ester hydrochloride (dry) in 150 ml of toluene with 245 ml of a 20% solution of phosgene in toluene after stirring for 6 hours at 110° C.) is added dropwise. The reaction mixture becomes reddish in hue and a solution forms, whereupon a precipitate forms again immediately. After a reaction time of 20 hours the solid is removed by filtration and the filtrate is concentrated by evaporation under reduced pressure. The residue, which contains the desired product in the form of the hydrochloride, is dissolved in 50 ml of water. The solution is adjusted to pH 2.5 by addition of phosphoric acid and extracted with methylene chloride. The aqueous phase is subsequently saturated with sodium chloride and extracted once more with methylene chloride. The residue of the second extract is crystallised from 10 ml of isopropanol and 50 ml of ethyl acetate at 4° C., affording 1,2-dimethyl-3-[(2(S)-methoxycarbonylpyrrolidino)carbonyloxy]-4(1H)-pyridinone which melts at 198°–200° C.

EXAMPLE 12

5.6 ml of triethylamine are added to a suspension of 5.56 g of 3-hydroxy-1,2-dimethyl-4(1H)-pyridinone in 400 ml of methylene chloride and 400 ml of acetonitrile, followed by the addition, over 30 minutes, of 7.38 ml of trimethylacetyl chloride. The reaction is complete after 15 minutes. The resultant solution is concentrated by evaporation under reduced pressure, the residue is taken up in water and extracted with methylene chloride. The residue of the organic extract is crystallised from 500 ml of ethyl acetate, affording 1,2-dimethyl-3- pivaloyloxy-4(1H)-pyridinone, which melts at 112°–113° C. (sinters from 103° C.).

The following compounds can be prepared in analogous manner:

3-(n-octanoyloxy)-1-(2-methoxyethyl)-2-methyl-4(1H)-pyridinone;

3-(ethoxycarbonyloxy)-1-(2-methoxyethyl)-2-methyl-4(1H)-pyridinone;

3-(diethylaminocarbonyloxy)-1-(2-methoxyethyl)-2-methyl-4(1H)-pyridinone;

3-[(2-ethoxycarbonylethyl)aminocarbonyloxy]-1-(2-methoxyethyl)-2-methyl-4(1H)-pyridinone;

3-(n-octanoyloxy)-1-(2-ethoxyethyl)-2-methyl-4(1H)-pyridinone;

3-(ethoxycarbonyloxy)-1-(2-ethoxyethyl)-2-methyl-4(1H)-pyridinone;

3-(diethylaminocarbonyloxy)-1-(2-ethoxyethyl)-2-methyl-4(1H)-pyridinone;

3-(ethoxycarbonylmethylaminocarbonyloxy)-1-(2-ethoxyethyl)-2-methyl-4(1H)-pyridinone; and 3-[(2-ethoxycarbonylethyl)aminocarbonyloxy]-1-(2-ethoxyethyl)-2-methyl-4(1H)-pyridinone.

EXAMPLE 13

Capsules containing 0.25 g of active ingredient, for example a compound of Examples 1–12, can be prepared as follows:

| Composition (for 1000 capsules:) | |
|---|---|
| active ingredient | 250 g |
| talcum | 36 g |
| corn starch | 24 g |
| magnesium stearate | 16 g |
| lactose | 4 g |
| | 330 g |

The powdered substances are passed through a 0.6 mm sieve and mixed. Portions of 0.33 g of the mixture are filled into gelatin capsules in a capsule filling machine.

What is claimed is:

1. A compound of formula

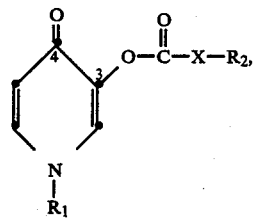

wherein $R_1$ is an unsubstituted or substituted hydrocarbon radical, X is a bond or a group of formula —O— or —N($R_3$)—, wherein $R_3$ is hydrogen or an unsubstituted or substituted hydrocarbon radical, and $R_2$ is an unsubstituted or substituted hydrocarbon radical, or wherein $R_2$ and $R_3$, when taken together, are an unsubstituted or substituted divalent hydrocarbon radical, and wherein the other ring carbon atoms of the 4(1H)-pyridinone ring, independently of one another, are unsubstituted or substituted by an unsubstituted or substituted hydrocarbon radical or by etherified or esterified hydroxy, or a salt of such compound having salt-forming properties.

2. A compound of formula I according to claim 1, wherein X is as defined in claim 1, $R_1$ and $R_2$ are each independently of the other alkyl, cycloalkyl, cycloalkenyl, cycloalkyl-lower alkyl, phenyl, naphthyl or phenyl-lower alkyl, which radicals are unsubstituted or substituted by hydroxy, lower alkoxy, lower alkanoyloxy, the radical of formula —O—C(=O)—X—$R_2$, wherein X and $R_2$ have the given meanings, and also by halogen, amino, lower alkylamino, di-lower alkylamino, carboxy, lower alkoxycarbonyl, carbamoyl, lower alkylcarbamoyl and/or di-lower alkylcarbamoyl, $R_3$ is hydrogen or lower alkyl, or wherein $R_1$ is as defined above, and $R_2$ and $R_3$, when taken together, are lower alkylene which is unsubstituted or substituted by hydroxy, lower alkoxy, lower alkanoyloxy, the radical of formula —O—C(=O)—X—$R_2$, wherein X and $R_2$ have the given meanings, and also by halogen, amino, lower alkylamino, di-lower alkylamino, carboxy, lower alkoxycarbonyl, carbamoyl, lower alkylcarbamoyl and/or di-lower alkylcarbamoyl, and wherein the other ring carbon atoms of the 4(1H)-pyridinone ring, independently of one another, are unsubstituted or are substituted preferably in the 2-or 6-position by alkyl, preferably lower alkyl, and alkyl, especially lower alkyl, can be substituted by hydroxy, lower alkoxy, esterified hydroxy of formula —O—C(=O)—X—$R_2$, wherein X and $R_2$ have the given meanings, and/or by halogen, or a salt of such compound having salt-forming properties.

3. A compound of formula I according to claim 1, wherein X is as defined in claim 1, $R_1$ is lower alkyl which is unsubstituted or is substituted in a position higher than 1-position by lower alkoxy, $R_2$ is lower alkyl which is unsubstituted or substituted by lower alkoxycarbonyl, and $R_3$ is hydrogen or lower alkyl, or wherein $R_1$ is as defined above, and $R_2$ and $R_3$, when taken together, are lower alkylene containing 4 or 5 carbon atoms in the chain which is unsubstituted or substituted by lower alkoxycarbonyl, and wherein the other ring carbon atoms of the 4(1H)-pyridinone ring, independently of one another, are unsubstituted or are substituted by lower alkyl which is unsubstituted or substituted by hydroxy, lower alkoxy, a radical of formula —O—(=O)—X—$R_2$, wherein X and $R_2$ have the given meanings, or by halogen, or a salt of such compound having salt-forming properties.

4. A compound of formula I according to claim 1, wherein $R_1$ is lower alkyl of up to 4 carbon atoms inclusive which may be substituted in a position higher than 1-position by lower alkoxy of up to 4 carbon atoms inclusive, and wherein X is a direct bond and $R_2$ is lower alkyl of 4 to 8 carbon atoms inclusive, or X is a group of formula —O— and $R_2$ is lower alkyl of up to 4 carbon atoms inclusive, or X is a group of formula —N($R_3$)—, wherein $R_3$ is hydrogen or lower alkyl of up to 4 carbon atoms inclusive, and $R_2$ is lower alkyl of up to 4 carbon atoms inclusive which is unsubstituted or substituted by lower alkoxycarbonyl of up to 5 carbon atoms inclusive, or wherein $R_2$ and $R_3$, when taken together, are lower alkylene containing 4 or 5 carbon atoms in the chain which is unsubstituted or substituted by lower alkoxycarbonyl of up to 5 carbon atoms inclusive, and wherein the 2-position is substituted by lower alkyl of up to 4 carbon atoms inclusive, or a salt of such compound having salt-forming properties.

5. 3-(Ethoxycarbonylmethylaminocarbonyloxy)-1,2-dimethyl-4(1H)-pyridinone or a salt thereof.

6. 1-Ethyl-3-(ethoxycarbonylmethylaminocarbonyloxy)-2-methyl-4(1H)-pyridinone or a salt thereof.

7. 3-(Ethoxycarbonylmethylaminocarbonyloxy)-1-(2-methoxyethyl)-2-methyl-4(1H)-pyridinone or a salt thereof.

8. 3-(Ethoxycarbonyloxy)-1,2-dimethyl-4(1H)-pyridinone,
3-(n-octanoyloxy)-1,2-dimethyl-4(1H)-pyridinone,
3-(diethylaminocarbonyloxy)-1,2-dimethyl-4(1H)-pyridinone,
3-[(2-ethoxycarbonylethyl)aminocarbonyloxy]-1,2-dimethyl-4(1H)-pyridinone,
3-(ethoxycarbonylmethylaminocarbonyloxy)-2-methyl-1-n-propyl-4(1H)-pyridinone,
3-(ethoxycarbonylmethylaminocarbonyloxy)-2-ethyl-1-methyl-4(1H)-pyridinone,
3-(ethoxycarbonylmethylaminocarbonyloxy)-1-(3-ethoxypropyl)-2-methyl-4(1H)-pyridinone,
1,2-dimethyl-3-[(2(S)-methoxycarbonylpyrrolidino)carbonyloxy]-4(1H)-pyridinone or
1,2-dimethyl-3-pivaloyloxy-4(1H)-pyridinone or salts thereof.

9. A pharmaceutically acceptable salt of a compound as claimed in claim 1 having salt-forming properties.

10. A pharmaceutical composition containing an effective chelating amount of a compound as claimed in claim 1.

11. A method of treating disease of pathological conditions of the human or animal body, associated with trivalent metal ion overload which comprises the use of a compound as claimed in claim 1.

* * * * *